United States Patent

Makaryk et al.

[11] Patent Number: 4,698,061
[45] Date of Patent: Oct. 6, 1987

[54] INJECTION SITE PACKAGE

[75] Inventors: Walter A. Makaryk, Mt. Prospect; Thomas E. Dudar, Palatine; Mary K. Zentz, Mundelein, all of Ill.

[73] Assignee: Baxter Travenol Laboratories, Inc., Deerfield, Ill.

[21] Appl. No.: 854,685

[22] Filed: Apr. 18, 1986

Related U.S. Application Data

[63] Continuation of Ser. No. 585,480, Mar. 2, 1984, abandoned.

[51] Int. Cl.⁴ .............................................. A61M 5/00
[52] U.S. Cl. ..................................... 604/408; 604/244
[58] Field of Search .................. 604/408, 86, 88, 204, 604/244, 262, 408, 409, 410; 128/DIG. 24; 222/80, 81; 427/208

[56] References Cited

U.S. PATENT DOCUMENTS

| | | | |
|---|---|---|---|
| 2,856,929 | 10/1958 | Gossett et al. | 604/408 |
| 3,205,889 | 9/1965 | Alder | 128/272 |
| 3,300,330 | 1/1967 | Vassel et al. | 427/208 |
| 3,306,563 | 2/1967 | Soto | 604/88 |
| 3,394,799 | 7/1968 | Ritson et al. | 427/208 |
| 3,683,911 | 8/1972 | McCormick | 128/DIG. 26 |
| 3,814,137 | 6/1974 | Martinez . | |
| 3,850,202 | 1/1974 | Morgan . | |
| 3,994,412 | 1/1976 | Difiglio . | |
| 4,273,827 | 6/1981 | Sweeney et al. | 427/208 |
| 4,279,352 | 7/1981 | Ward . | |
| 4,324,236 | 4/1982 | Gordon et al. | 604/180 |
| 4,390,104 | 6/1983 | Cummings | 604/408 |

Primary Examiner—Stephen C. Pellegrino
Attorney, Agent, or Firm—Paul C. Flattery; Daniel D. Ryan

[57] ABSTRACT

An injection site package for application to a plastic wall. A resealable rubber injection site carries first adhesive on one face. A first overlay is carried on the first adhesive to cover it, the first overlay having release properties to be peelable from the first adhesive. A second overlay is carried to cover the face of the injection site opposed to the one face, and the second overlay is removable from the opposed face.

7 Claims, 6 Drawing Figures

INJECTION SITE PACKAGE

This application is a continuation, of application Ser. No. 585,480, filed Mar. 2, 1984 now abandoned.

TECHNICAL FIELD AND PRIOR ART

This application relates to an injection site which can function as an access port to insert or withdraw materials from a sterile medical container, for example, without the use of an actual tubular port carried on the container.

Parenteral solution containers, blood bags, and other containers are in widespread medical use, containing tubular access ports of many and various kinds, to provide substantially sterile access to the container. Likewise, conventional ampules for hypodermic needles often utilize a rubber diaphragm over the mouth of the ampule, which is penetrated by the hypodermic needle to obtain access to the contents thereof. As is well known, when the needle is withdrawn the rubber diaphragm reseals, providing effective resealing of the container as long as there is not a significant pressure differential between the interior and exterior of the ampule.

It is, of course, well known to make use of rubber membranes in other forms to provide injection sites. For example, Martinez U.S. Pat. No. 3,814,137, Ward U.S. Pat. No. 4,279,352, and Morgan U.S. Pat. No. 3,850,202 give examples of various rubber diaphragm injection sites, all of which are used in conjunction with tubular conduits. Similarly, while many other designs of injection sites are used in the various fluid containers in the medical field, they generally are used in conjunction with tubular ports as well.

Tubular access ports may be separately formed and then placed upon the container by adhesion as shown, for example, in Alder et al. U.S. Pat. No. 3,205,889 and Difiglio U.S. Pat. No. 3,994,412.

In accordance with this invention, an injection site is provided for access to a container without reference to any tubular port. This provides a significant increase in flexibility of use of the device, as well as decreased cost of manufacture, since the cost of the tubular port and its installation is eliminated. At the same time, the user is free to apply the injection site of this invention to any desired needle-piercebale plastic wall, typically a flexible plastic wall of a solution container, to provide any desired number of injection sites on the container at any desired location.

DESCRIPTION OF THE INVENTION

In accordance with this invention, an injection site package is provided for application of the injection site contained therein to a plastic wall. The injection site comprises a resealable rubber injection site carrying first adhesive on one face thereof. Typically the injection site is flat and sheetlike, being a disc or rectangle, for example, of resealable rubber sheeting. Typically, polyisoprene rubber is a preferred form of resealable rubber, although any desired resealable rubber may be used, including a thermoplastic rubber material such as KRATON ®, sold by the Shell Chemical Company.

A first overlay is carried on the first adhesive to cover the first adhesive and one face of the rubber injection site. The first overlay has release properties so as to be peelable from the first adhesive. Typically, the first overlay may be made of a commercially available release paper to provide these release properties.

A second overlay is carried to cover the face of the injection site opposed to the one face, the second overlay being removable from the opposed face. Typically the second overlay adheres to the opposed face with a relatively light duty adhesive to permit such removal. In contrast, the first adhesive is typically a relatively permanent adhesive which, of course, does not adhere strongly to the first overlay because of the release characteristics of the first overlay.

The first and second overlays may be releasably peripherally joined together to sealingly enclose the injection site. This preserves its sterility. At the same time, tab means or other gripper means may be provided to permit the separation of the peripheral seal between the first and second overlays for access to the injection site.

In use, the first overlay is removed from the first adhesive coated face of the injection site. The first adhesive coated face is then applied to the flexible plastic wall, typically after cleaning the appropriate portion of the plastic wall with antiseptic prior to adhering the first adhesive coated face to it.

Thereafter, when one wishes to make use of the injection site, one can peel away the second overlay from the injection site. The light duty adhesive, holding the second overlay to the injection site, is formulated to be weaker than the relatively permanent adhesive now in relatively permanent bonding with the plastic wall, so the second overlay is easily removed without separating the injection site from the plastic wall. The newly exposed, opposed face of the injection site can be sterile, and thus provides a sterile injection site for needle access through the plastic wall.

DESCRIPTION OF SPECIFIC EMBODIMENTS

Figure 1:
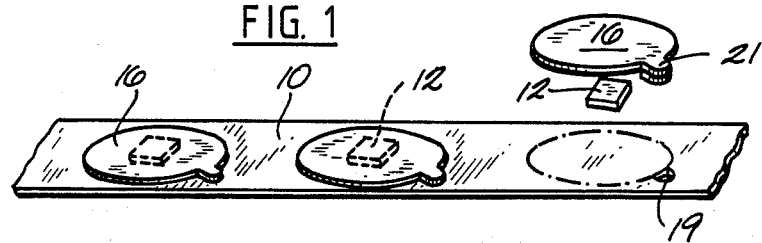
FIG. 1 is a plan view of an injection site package of this invention, with an exploded portion, in which the first overlay is a long strip carrying a plurality of associated rubber injection sites and second overlays.
Figure 2:
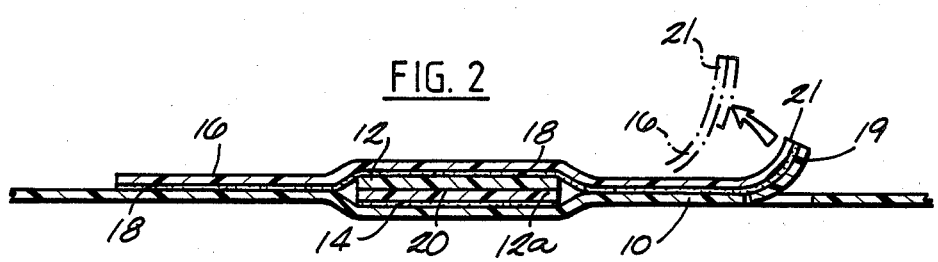
FIG. 2 is a fragmentary, sectional view showing one of the resealable rubber injection sites, and its second overlay being removed from the first overlay.

Referring to FIG. 1, an injection site package is disclosed which may be part of a long first overlay strip 10 wound on a roll. Accordingly, many injection sites may be provided in a single package, being held, for example, in a convenient dispenser so that the user can simply remove the injection sites one by one for use. First overlay 10 is shown to be a sheet of release paper, for example 3M release paper. Rectangular pieces 12 of natural rubber latex or other rubber in flat sheet form, typically having a thickness of about 0.03 inch, are provided to first overlay 10 as injection sites, the injection sites 12 being spaced from each other along sheet 10. As shown in FIG. 2, each injection site 12 carries on its lower face a coating of relatively permanent adhesive 14. A typical adhesive that may be used is a 3M hypoallergenic medical grade adhesive. This adhesive could contain an antimicrobial agent such as methyl propyl paraben that would eliminate or reduce the need to clean the appropriate portion of the plastic wall with antiseptic.

Each flat rubber injection site 12 is covered with a second overlay 16, adhering to injection site 12 by adhesive coating 18. Adhesive coating 18 is a relatively light duty adhesive, having less tack than adhesive 14, and also available from the 3M Company as a hypoallergenic medical grade adhesive. Second overlay 16 may be polyester film. There is preferably sufficient adhesive bonding in the area of the joined overlays 10, 16 peripheral to injection site 12 that the injection site is sealed and kept in sterile condition following sterilization by the manufacturer, typically radiation sterilization, for example gamma ray or electron beam sterilization. Alternatively, overalsy 10, 16 may be peripherally heat sealed or otherwise glued together.

A portion 19 of overlay 10 may be cut on all sides under pull tab 21 and permanently bonded to tab 21, for ease of manual access to pull the tab 21, to facilitate hand removal of each overlay 16.

As specifically shown, injection site 12 may have a second separate layer of latex 12a which is separate from and bonded to injection site 12 by use of an adhesive at their junction faces 20. It has been found that the use of a plurality of overlying, resealable rubber injection sites provides improved resealing of the needle puncture holes when compared with a single thickness resealable rubber injection site of the same thickness as the two layers 12, 12a. However, for purposes of economy and other reasons, a single-layer injection site may be used in accordance with this invention.

Figure 3:
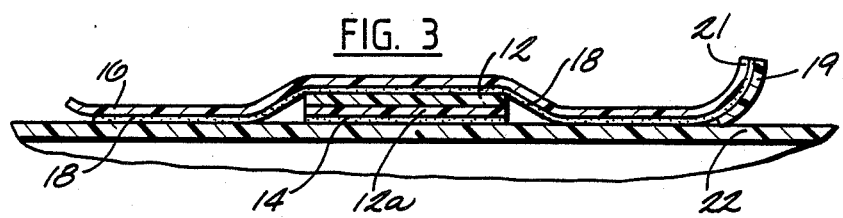
FIG. 3 is a sectional view of the injection site of FIG. 2 shown applied to a plastic wall.

As shown in FIG. 2 in phantom, second overlay 16 and site 12 may be peeled away from first overlay 10 to expose the relatively permanent adhesive coating 14. The bond of light duty adhesive 18 between injection site 12 and second overlay 16 causes these two members to remain together as they are pulled away from release paper 10. They may then be placed upon the wall 22 of a medical solution container or the like as shown in FIG. 3 with adhesive 14 bonding to wall 22. If the appropriate area of the outer surface of wall 22 has been sterilized with an alcohol or povidone iodine scrub, the system as shown in FIG. 3 can remain substantially sterile.

Figure 4:
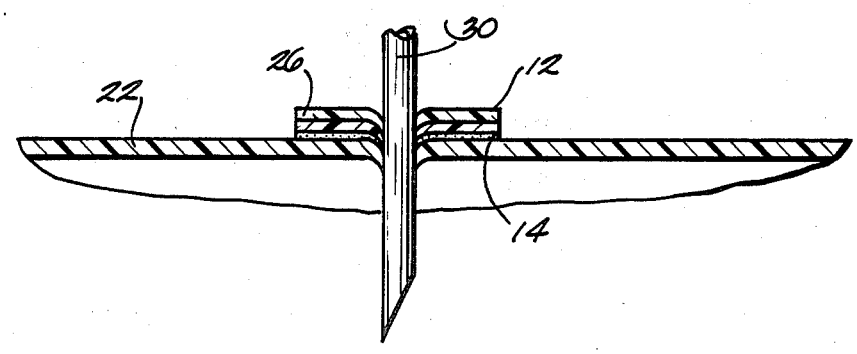
FIG. 4 shows the injection site of FIG. 3 with the second overlay removed, the injection site being in use.

Thereafter, as shown in FIG. 4, second overlay 16 is peeled away, typically taking adhesive layer 18 with it. This can be engineered by having the adhesive layer 18 more compatible with the material of second overlay 16 than the rubber material of injection site 12. The newly exposed upper surface 26 of injection site 12 can be sterile, and thus may not require an alcohol swab. An injection needle 30 can then penetrate injection site 12 to either administer or collect contents within the container wall 22.

After withdrawal of needle 30, injection site 12 reseals itself again in the manner of a conventional hypodermic needle ampule, for example, to avoid leakage of the contents held within container wall 22.

Figure 5:
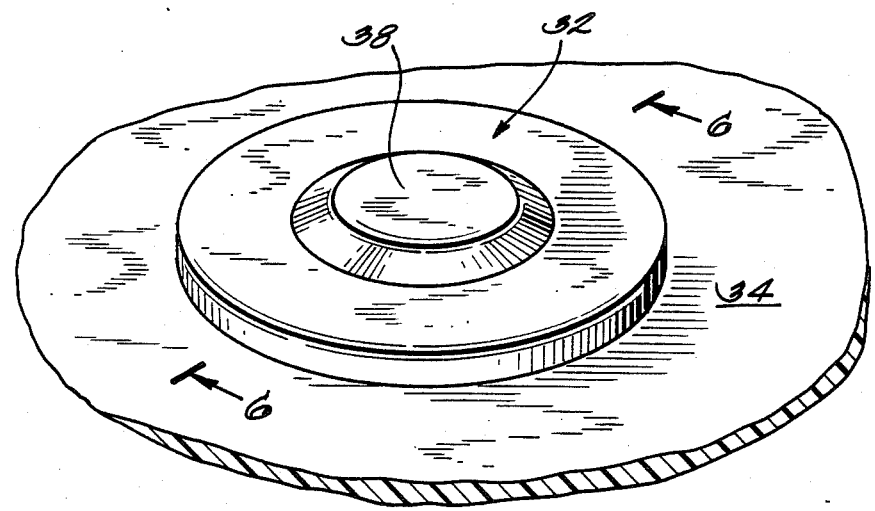
FIG. 5 shows another embodiment of needle pierceable injection site applied to a plastic wall in accordance with this invention and ready for use.

Turning to FIG. 5, a different design of injection site 32 is shown in adhering relationship to a container wall 34. Injection site 32 may be initially contained in a package in a manner similar to the package of FIGS. 1-4. Alternatively, injection site 12, injection site 32, or any other desired injection site may be separately packaged, with the first overlay being not a strip but a square or other shape of approximately the same size as the second overlay, and typically initially in peripheral adhering relation with the second overlay.

Figure 6:
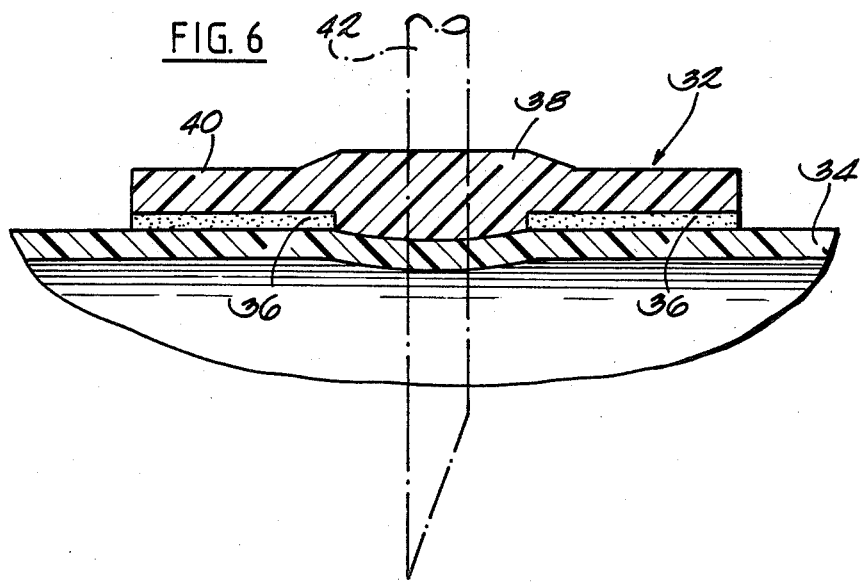
FIG. 6 is a sectional view taken along line 6—6 of FIG. 5 showing needle penetration of the injection site.

FIGS. 5 and 6 show injection site 32 after removal of the first and second overlays, with relatively permanent adhesive 36 being provided in the form of a ring in this embodiment, so that the thickened central portion 38 of injection site 32 does not carry any adhesive. The thickening of central portion 38 provides the advantage of improved resealability, while rubber is saved by the use of thinner peripheral portions 40 where no needle puncture is intended. At the same time, the absence of adhesive underneath thickened portion 38 provides the opportunity for a penetrating needle 42 not to encounter an adhesive layer as it penetrates into the container. Because of this, any possible toxicity questions relative to adhesive layer 36 can be avoided, since a needle puncture through the thickened area 38 will not enter into contact with adhesive 36. There is thus no chance of any accidental penetration of adhesive into the container on the tip of the needle 42. The contents enclosed by wall 34 remain entirely isolated from the adhesive.

Accordingly, by this invention a port-free injection site is provided. The injection site may be applied to any container having a needle-pierceable wall, for greatly facilitated procedures both in the medical field and in any other desired field of endeavor, for example biochemistry or the handling of radioactive or toxic materials.

The above has been offered for illustrative purposes only, and is not intended to limit the scope of the invention of this application, which is as defined in the claims below.

That which is claimed is:

1. An injection site package which can be attached to a needle-pierceable wall, said package comprising;
a resealable rubber injection pad having opposite first and second pad faces,
a first overlay covering sad first pad face,
a second overlay covering said second face pad,
first adhesive means at least partly covering said first pad face for removably joining said first overlay and said first pad face and for permitting separation of said first overlay from said first pad face upon the application of a peeling force, said first adhesive means being further operative, upon separation of said first overlay, for joining said first pad face and the needle-pierceable wall,
second adhesive means at least partly covering said second face for removably joining said second overlay and said second pad face and for permitting separation of said first overlay and said second adhesive means from said second pad face upon the application of a peeling force,
said first overlay being separable from said first pad face without separating said second overlay from said second pad face as a peeling force is applied to said second overlay, thereby exposing said first pad face for joining the needle-pierceable wall, and
said second overlay and said second adhesive means being separable from said second pad face without separating said first pad face from the needle-pierceable wall as a peeling force is applied to said second overlay, thereby exposing said second pad face to the needle used to pierce the needle-pierceable wall.

2. An injection site package according to claim 1 wherein said second adhesive means is more compatible with the material of said second overlay than with the material of said second pad face so that, as said second overlay is removed from said second pad face, said second adhesive means adheres to said second overlay for removal therewith.

3. An injection site package according to claim 1 wherein said pad includes peripheral edges,
wherein, when said second overlay covers said second pad face, said second overlay has peripheral edges which extend beyond said peripheral edges of said pad, and
wherein said second adhesive means joins said peripheral edges of said second overlay to said first overlay with an adhesive bond which seals said pad within said first and second overlays and which permits separation of said peripheral edges of said second overlay from said first overlay as said first overlay is separated from said first pad face.

4. An injection site package according to claim 1 wherein said pad includes peripheral edges, and
wherein said first adhesive means is located on said peripheral edges of said first pad face, the remainder of said first pad face being essentially free of said first adhesive means.

5. An injection site package according to claim 4 wherein said pad includes a thickened central portion for piercing by the needle used to pierce the needle-pierceable wall.

6. An injection site package according to claim 1 wherein said first adhesive means includes an antimicrobial agent.

7. An injection site package according to claim 1 with said pad formed of first and second adjacent layers.

* * * * *